United States Patent
Pu et al.

(10) Patent No.: US 9,084,792 B2
(45) Date of Patent: Jul. 21, 2015

(54) METHOD FOR PREPARING ACYCLOVIR 2/3 HYDRATE

(75) Inventors: Tong Pu, Zhejiang (CN); Yi Fan, Zhejiang (CN); Tian Chen, Zhejiang (CN); Ming Lei, Zhejiang (CN); Naixing Wang, Zhejiang (CN); Zhen Yang, Zhejiang (CN); Jianming Yang, Zhejiang (CN)

(73) Assignee: Zhejiang Charioteer Pharmaceutical Co., Ltd., Zhejiang (CN)

( * ) Notice: Subject to any disclaimer, the term of this patent is extended or adjusted under 35 U.S.C. 154(b) by 472 days.

(21) Appl. No.: 13/259,466

(22) PCT Filed: Mar. 17, 2010

(86) PCT No.: PCT/CN2010/071087
§ 371 (c)(1),
(2), (4) Date: Sep. 23, 2011

(87) PCT Pub. No.: WO2010/108417
PCT Pub. Date: Sep. 30, 2010

(65) Prior Publication Data
US 2012/0010408 A1    Jan. 12, 2012

(30) Foreign Application Priority Data
Mar. 27, 2009   (CN) .......................... 2009 1 0097244

(51) Int. Cl.
*C07D 473/18*   (2006.01)
*A61K 31/522*   (2006.01)

(52) U.S. Cl.
CPC ............ *A61K 31/522* (2013.01); *C07D 473/18* (2013.01)

(58) Field of Classification Search
CPC ............................ C07D 473/18; A61K 31/522
USPC ....................................................... 544/276
See application file for complete search history.

(56) References Cited

FOREIGN PATENT DOCUMENTS

| CN | 101245068 A | 8/2008 | | |
|---|---|---|---|---|
| CN | 101602764 A | 12/2009 | | |
| EP | 1 746 098 A1 | 1/2007 | | |
| ES | 2047457 A1 | * 2/1994 | ............. | A61K 31/52 |
| WO | WO-2009/031576 A1 | 3/2009 | | |

OTHER PUBLICATIONS

Coto, A.D., ES 2047457, Feb. 16, 1994, Partial English Translation (p. 5, lines 24-36).*
Terada, K., Polymorphic and pseudopolymorphic transformation behavior of acyclovir based on thermodynamics and crystallography, (2013) J. Therm. Anal. Calorim. 113, 1261-1267.*
Dash, A. K., Solid State Characterization of AG337 (Thymitaq), a Novel Antitumor Drug, (1996) J. Pharm. Sci. 85 (10), 1123-1127.*
Armarego, W. L. F., Purification of Laboratory Chemicals, Fifth Edition, Butterworth Heinemann, 2003, Chapter 1, p. 1-30.*
Thermo ARL Basics of X-ray Diffraction, Introduction of Powder Polycrystalline Diffraction, ARL Applied Research Laboratories S.A.1999, p. 1-22.; https://www.google.com/#newwindow=1&q=introduction+xrpd+diffraction+angle+pdf.*
Birnbaum, G. et al. "Conformational features of acyclonucleosides: structure of acyclovir, an antiherpes agent" *Can. J. Chem.*, 1984, 62:2646-2652.
Kristl, A. et al. "Polymorphism and pseudopolymorphism: influencing the dissolution properties of the guanine derivative acyclovir" *International Journal of Pharmaceutics*, 1996, 139:231-235.
Sohn, Y.T. et al. "Polymorphism and Pseudopolymorphism of Acyclovir" *Archives of Pharmacal Research*, 2008, 31(2):231-234.

* cited by examiner

*Primary Examiner* — Noble Jarrell
*Assistant Examiner* — John Mauro
(74) *Attorney, Agent, or Firm* — Saliwanchik, Lloyd & Eisenschenk

(57) ABSTRACT

Preparation of acyclovir 2/3 hydrate comprises mixing acyclovir with water at weight ratio of 1:5~50, dissolving at 50~100° C., filtering, cooling filtrate at 0~30° C. to precipitate crystal, collecting the crystal by filtration, and drying the crystal at 0~150° C. for 0.5~24 hours to obtain acyclovir 2/3 hydrate. The preparation process is simple and suitable for industrial production. The prepared product has good and stable crystal form.

8 Claims, 4 Drawing Sheets

METHOD FOR PREPARING ACYCLOVIR 2/3 HYDRATE

CROSS-REFERENCE TO RELATED APPLICATIONS

This application is the U.S. national stage application of International Patent Application No. PCT/CN2010/071087, filed Mar. 17, 2010, which claims priority to Chinese Application No. 200910097244.5, filed Mar. 27, 2009, the disclosures of each of which are incorporated herein by reference in their entirety.

TECHNICAL FIELD

The present invention relates to the preparation of a nucleoside drug acyclovir (ACV) 2/3 hydrate.

BACKGROUND ART

Acyclovir is a new HBV-DNA polymerase inhibitor, having broad spectrum antiviral activity against animal and human viruses.

Kristl (Int. J. Phar. 1996, 139, 231-235) reported some crystal forms of acyclovir, including 2/3 hydrate, instable anhydrous form and anhydrous (stable) form 1 and anhydrous form 2. The results showed that, compared with other forms, 2/3 hydrate had higher water solubility and thus higher bioavailability, and was suitable for preparing antiviral preparations. The acyclovir in European Pharmacopeia is 2/3 hydrate. However, the preparation process and XRD data of acyclovir 2/3 hydrate have not been reported yet. Young (Arch. Pharm. Res. 2008, 31, 231-234) disclosed an acyclovir hydrate (Form 3), which had a weight-loss as measured by Thermogravimetric Analysis (TGA) of about 6.74%.

SUMMARY OF THE INVENTION

The technical problem of the present invention to solve is to provide a method for preparing acyclovir 2/3 hydrate (i.e. ACV 2/3 hydrate), which is simple and suitable for industrial production.

In order to solve the above technical problem, the invention adopts the following technical scheme:

A method for preparing acyclovir 2/3 hydrate comprises: mixing acyclovir with water at weight ratio of 1:5~50, dissolving at 50~100° C., filtering, cooling filtrate to 0~30° C. to precipitate crystal, collecting the crystal by filtration, and drying the crystal at 0~150° C. for 0.5~24 hours to obtain acyclovir 2/3 hydrate.

In the dry step of the present invention, the drying conditions should be controlled properly in order to obtain qualified acyclovir 2/3 hydrate with water content of 5.1% by weight. One of ordinary skill in the art can carry out the dry step in a conventional manner to obtain acyclovir 2/3 hydrate. For example, if the dry step is carried out at high temperature (for example, over 100° C.) and lasts a longer time, the crystal is easy to lose too much water and thus the water content may be below 5.1%. Generally, when the water content of the crystal gets to be below 5.1% after drying, the crystal can be placed under the circumstance of 60~80% relative humidity of air for 8~10 hours to obtain acyclovir 2/3 hydrate. Vacuum can be adopted to improve drying efficiency.

In the present invention, the time required for precipitating crystal is 1~24 hours.

Further, acyclovir and water are preferably mixed at weight ratio of 1:10~15.

Preferably, the filtrate is cooled to 20~30° C. and held for 4~10 hours to precipitate crystal.

Preferably, the crystal is dried at 50~100° C. for 5-12 hours to obtain acyclovir 2/3 hydrate.

In the present invention, it is recommended to carry out the preparation of acyclovir 2/3 hydrate as follows: acyclovir and water are mixed at weight ratio of 1:5~50 and dissolved at 50~100° C. Then the mixture is filtered. The filtrate is cooled to 20~30° C. and held for 4~10 hours to precipitate crystal. The crystal is collected by filtration, and then dried at 50~100° C. for 5~12 hours to obtain the acyclovir 2/3 hydrate.

The acyclovir 2/3 hydrate according to the present invention shows the following characteristic peaks expressed in terms of 2θ and interplanar spacings (d value) in the X-ray powder diffraction pattern obtained with Cu-Kα radiation:

| Peak | 2θ(°) | interplanar spacing d(Å) |
|---|---|---|
| 1 | about 7.0 | about 12.7 |
| 2 | about 10.5 | about 8.4 |
| 3 | about 13.1 | about 6.8 |
| 4 | about 16.1 | about 5.5 |
| 5 | about 18.3 | about 4.9 |
| 6 | about 21.0 | about 4.2 |
| 7 | about 24.9 | about 3.7 |
| 8 | about 26.2 | about 3.4 |
| 9 | about 29.2 | about 3.0 |

The acyclovir 2/3 hydrate according to the present invention shows absorption peaks at about 3522 $cm^{-1}$, about 3471 $cm^{-1}$, about 3438 $cm^{-1}$, about 3294 $cm^{-1}$, about 3180 $cm^{-1}$, about 2854 $cm^{-1}$, about 2698 $cm^{-1}$, about 1716 $cm^{-1}$, about 1631 $cm^{-1}$, about 1610 $cm^{-1}$, about 1483 $cm^{-1}$, about 1388 $cm^{-1}$, about 1182 $cm^{-1}$, about 1105 $cm^{-1}$, about 1049 $cm^{-1}$, and about 902 $cm^{-1}$ in the infrared absorption spectrum (KBr pellet).

The acyclovir 2/3 hydrate according to the present invention has a weight-loss as measured by Thermogravimetric Analysis (TGA) of 5.1% by weight.

The preparation process of the present invention is simple and suitable for industrial production. The acyclovir 2/3 hydrate according to the present invention has the following advantages:

(1) It has the property required for large-scale preparation of drugs: for example, it has thermal decomposition point of over 250° C., and good fluidity and bulk density, which are in favor of drug preparation and industrial production on a large scale.

(2) It has good stability of crystalline form. The stability test has shown that the acyclovir 2/3 hydrate obtained according to the present invention can he stored for more than one year at room temperature with relative humidity of less than 50%. During the storage time, the crystalline form remains the same and the content does not reduce, which completely comply with the European Pharmacopoeia specification. It can be stored in the dark, cool and dry place for a long time.

DESCRIPTION OF THE PREFERRED EMBODIMENT

Figure 1:
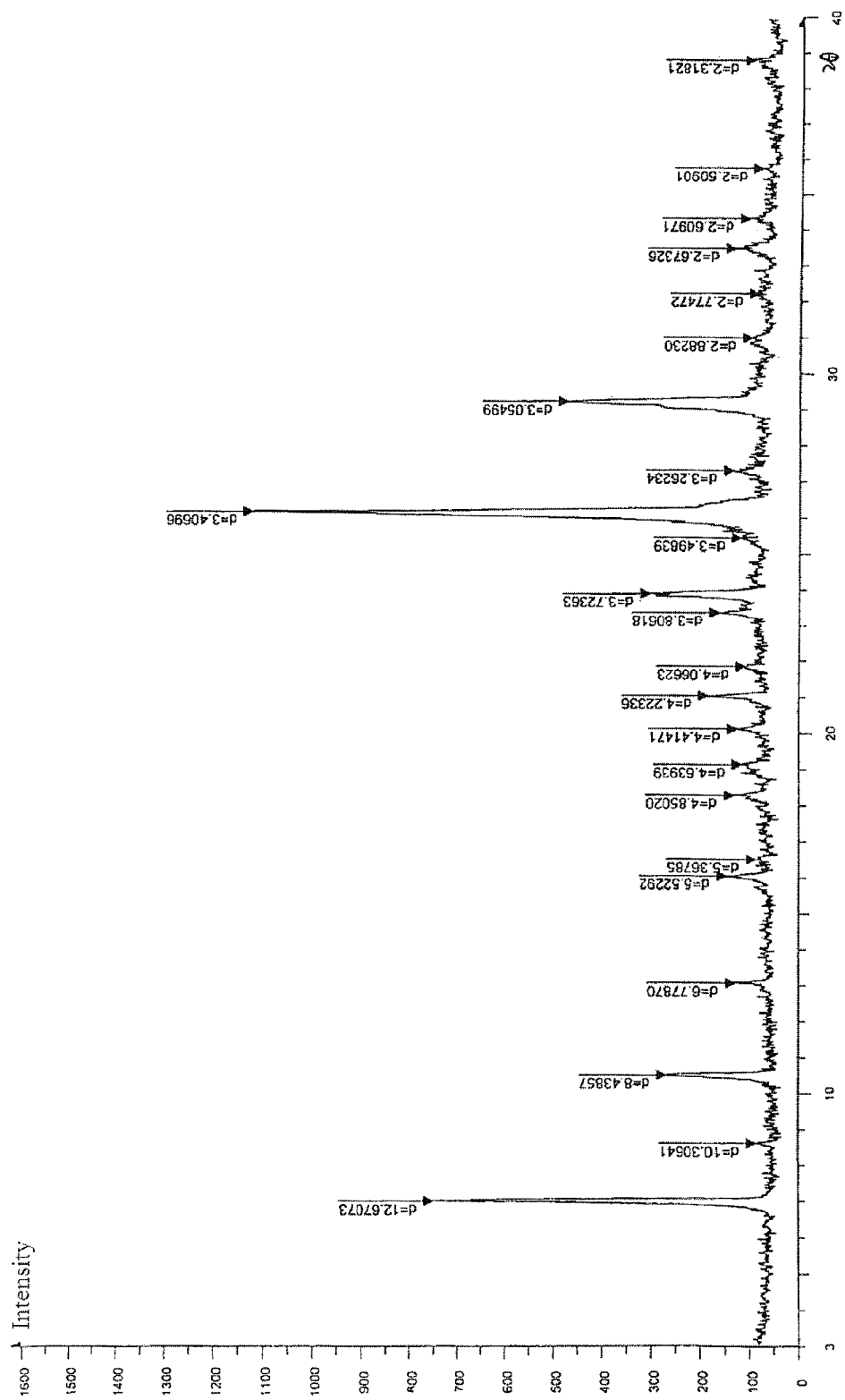
FIG. 1 shows the X-ray powder diffraction pattern of ACV 2/3 hydrate according to the present invention.
Figure 2:
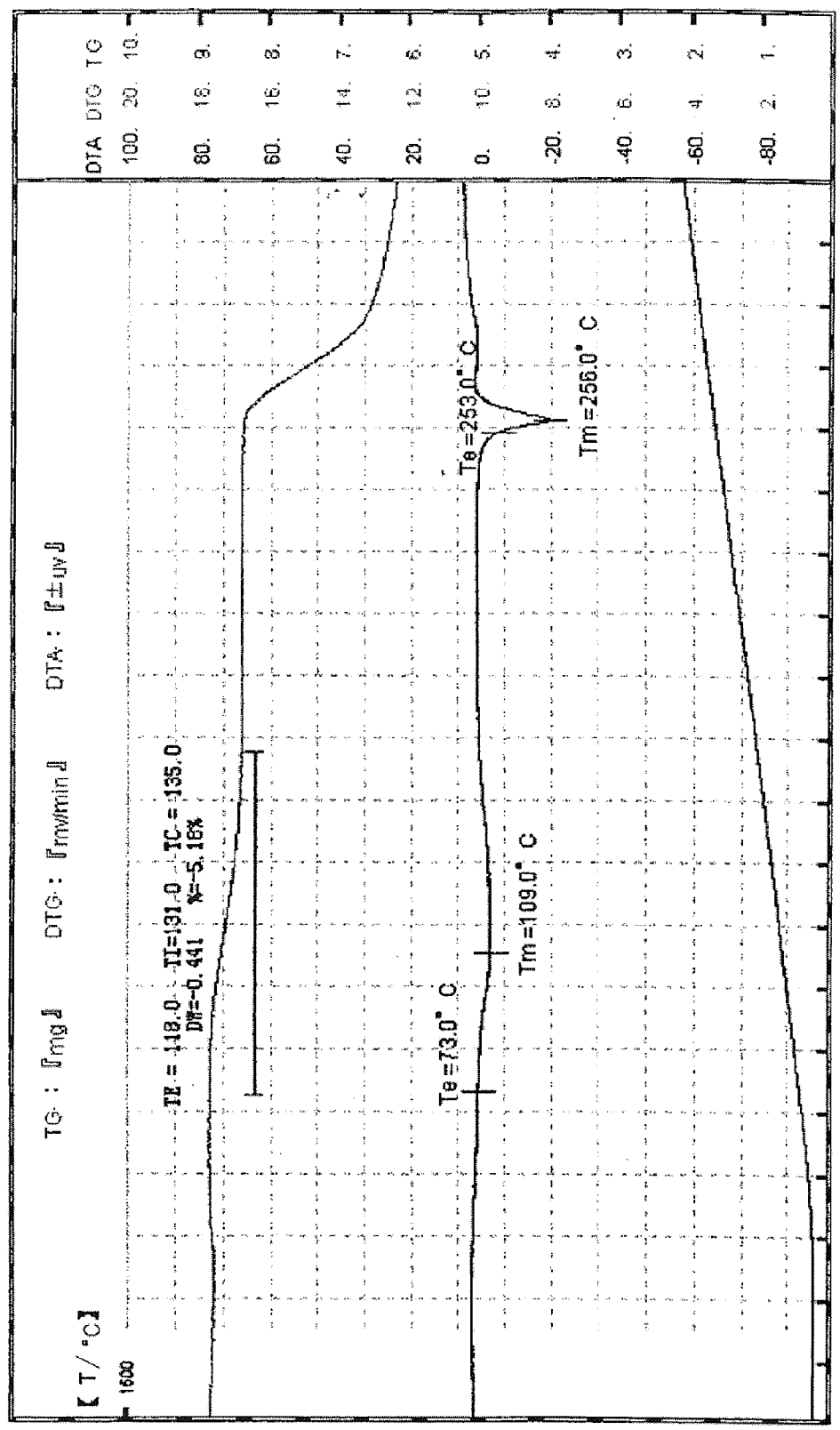
FIG. 2 shows the TGA spectrum of ACV 2/3 hydrate according to the present invention.
Figure 3:
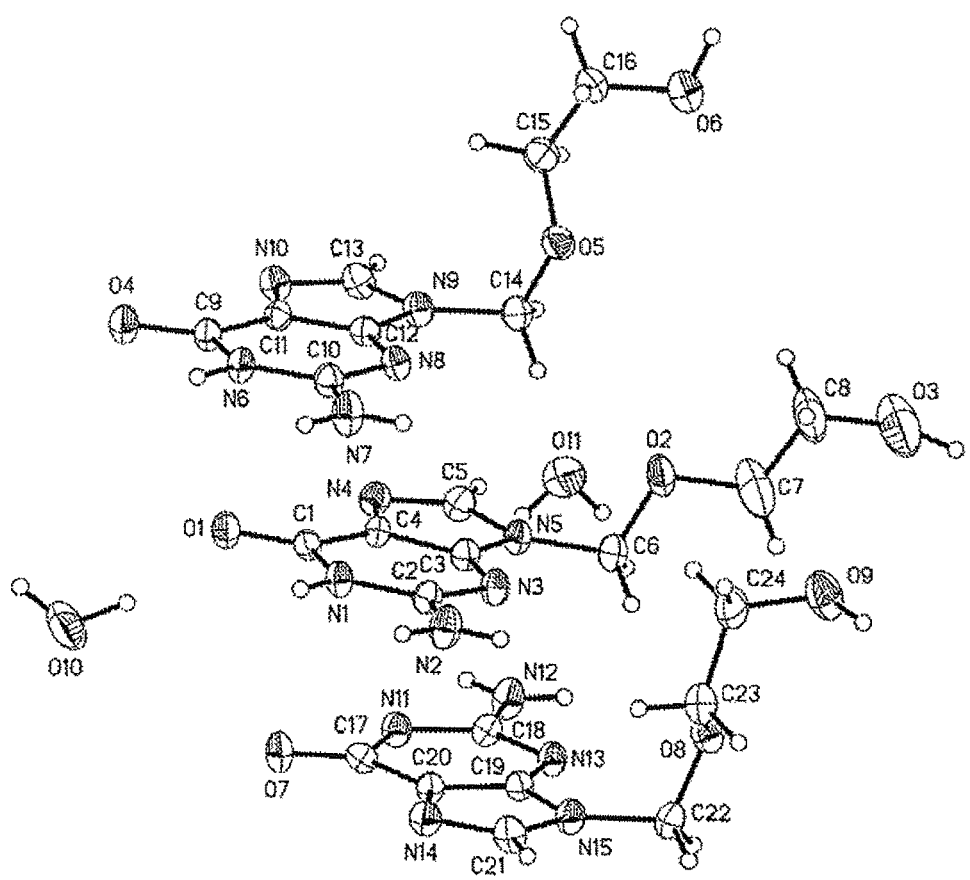
FIG. 3 shows the single-crystal X-ray diffraction spectrum of ACV 2/3 hydrate according to the present invention.
Figure 4:
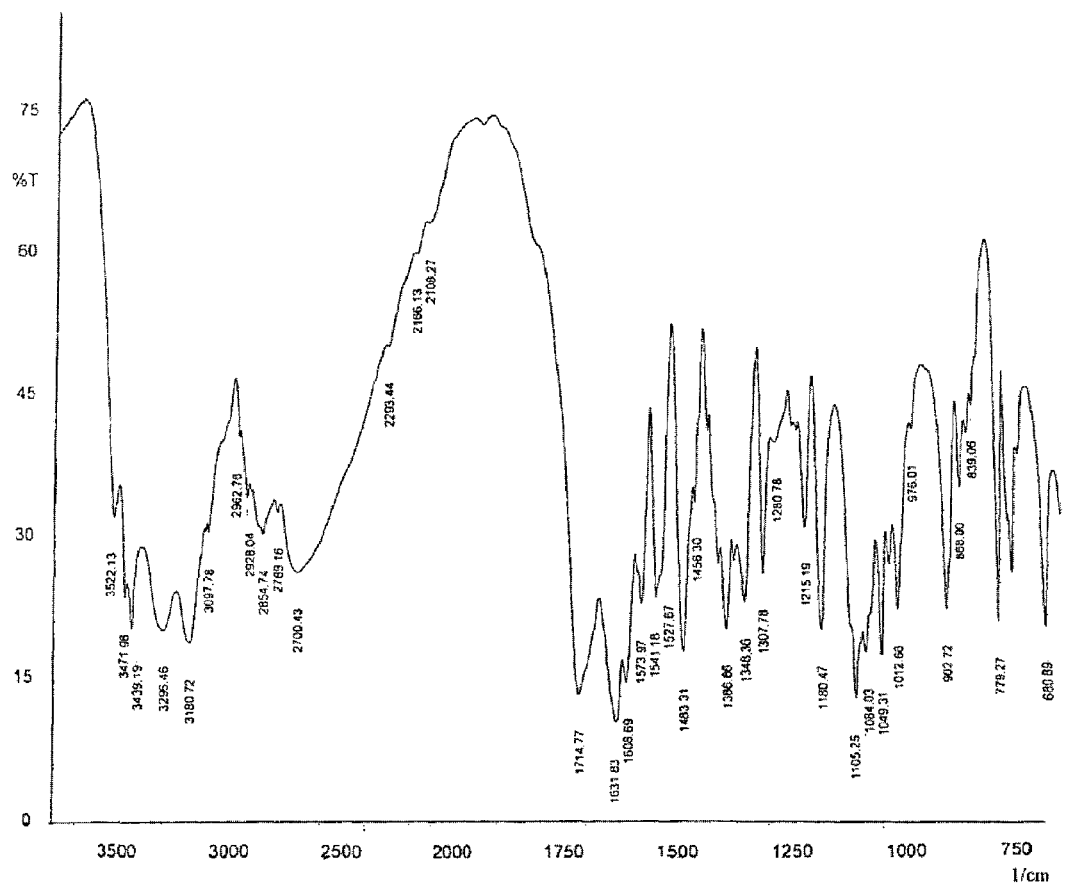
FIG. 4 shows the infrared absorption spectrum of ACV 2/3 hydrate according to the present invention.

Following are examples, which illustrate the present invention in detail. These examples should not be construed as limiting.

Example 1

The mixture of acyclovir (10 g) and water (120 ml) was heated to 95° C., stirred to obtain a clear solution, and filtered. The filtrate was cooled to 20~25° C., held for 5 h to precipitate crystal and then filtered. The resulting solid was dried under vacuum at 50° C. for 20 h to obtain acyclovir crystal (9.8 g), with purity of 99.6% by HPLC. The solid was ground into powder of 200 mesh in size. The X-ray powder diffraction pattern of the product obtained with Cu-Kα radiation exhibited characteristic peaks at 2θ and interplanar spacings (d value) of about 7.0(12.7), about 10.5(8.4), about 13.1(6.8), about 16.1(5.5), about 18.3(4.9), about 21.0(4.2), about 24.9 (3.7), about 26.2(3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 cm$^{-1}$, about 3471 cm$^{-1}$, about 3438 cm$^{-1}$, about 3294 cm$^{-1}$, about 3180 cm$^{-1}$, about 2854 cm$^{-1}$, about 2698 cm$^{-1}$, about 1716 cm$^{-1}$, about 1631 cm$^{-1}$, about 1610 cm$^{-1}$, about 1483 cm$^{-1}$, about 1388 cm$^{-1}$, about 1182 cm$^{-1}$, about 1105 cm$^{-1}$, about 1049 cm$^{-1}$, and about 902 cm$^{-1}$.

Example 2

The mixture of acyclovir (10 g) and water (150 ml) was heated to 90° C., stirred to obtain a clear solution and filtered. The filtrate was cooled to 20~25° C., held for 5 h to precipitate crystal, and then filtered. The resulting solid was dried under vacuum at 50° C. for 20 h to obtain acyclovir crystal (9.6 g), with purity of 99.7% by HPLC. The solid was ground into power of 200 mesh in size. The X-ray powder diffraction pattern of the product obtained with Cu-Kα radiation exhibited characteristic peaks at 2θ and interplanar spacings (d value) of about 7.0(12.7), about 10.5(8.4), about 13.1(6.8), about 16.1(5.5), about 18.3(4.9), about 21.0(4.2), about 24.9 (3.7), about 26.2(3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 cm$^{-1}$, about 3471 cm$^{-1}$, about 3438 cm$^{-1}$, about 3294 cm$^{-1}$, about 3180 cm$^{-1}$, about 2854 cm$^{-1}$, about 2698 cm$^{-1}$, about 1716 cm$^{-1}$, about 1631 cm$^{-1}$, about 1610 cm$^{-1}$, about 1483 cm$^{-1}$, about 1388 cm$^{-1}$, about 1182 cm$^{-1}$, about 1105 cm$^{-1}$, about 1049 cm$^{-1}$, and about 902 cm$^{-1}$.

Example 3

The mixture of acyclovir (10 g) and water (200 ml) was heated to 90° C., stirred to obtain a clear solution and filtered. The filtrate was cooled to 20~25° C., held for 10 h to precipitate crystal and then filtered. The resulting solid was dried under vacuum at 50° C. for 20 h to obtain acyclovir crystal (9.5 g), with purity of 99.7% by HPLC. The solid was ground into power of 200 mesh in size. The X-ray powder diffraction pattern of the product obtained with Cu-Kα radiation exhibited characteristic peaks at 2θ and interplanar spacings (d value) of about 7.0(12.7), about 10.5(8.4), about 13.1(6.8), about 16.1(5.5), about 18.3(4.9), about 21.0(4.2), about 24.9 (3.7), about 26.2(3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 cm$^{-1}$, about 3471 cm$^{-1}$, about 3438 cm$^{-1}$, about 3294 cm$^{-1}$, about 3180 cm$^{-1}$, about 2854 cm$^{-1}$, about 2698 cm$^{-1}$, about 1716 cm$^{-1}$, about 1631 cm$^{-1}$, about 1610 cm$^{-1}$, about 1483 cm$^{-1}$, about 1388 cm$^{-1}$, about 1182 cm$^{-1}$, about 1105 cm$^{-1}$, about 1049 cm$^{-1}$, and about 902 cm$^{-1}$.

Example 4

The mixture of acyclovir (10 g) and water (200 ml) was heated to 90° C., stirred to obtain a clear solution and filtered. The filtrate was cooled to 20~25° C., held for 10 h to precipitate crystal, and then filtered. The resulting solid was dried at 70° C. for 20 h to obtain acyclovir crystal (9.5 g), with purity of 99.5% by HPLC. The solid was ground into power of 200 mesh in size. The X-ray powder diffraction pattern of the product obtained with Cu-Kα radiation exhibited characteristic peaks at 2θ and interplanar spacings (d value) of about 7.0(12.7), about 10.5(8.4), about 13.1(6.8), about 16.1(5.5), about 18.3(4.9), about 21.0(4.2), about 24.9(3.7), about 26.2 (3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 cm$^{-1}$, about 3471 cm$^{-1}$, about 3438 cm$^{-1}$, about 3294 cm$^{-1}$, about 3180 cm$^{-1}$, about 2854 cm$^{-1}$, about 2698 cm$^{-1}$, about 1716 cm$^{-1}$, about 1631 cm$^{-1}$, about 1610 cm$^{-1}$, about 1483 cm$^{-1}$, about 1388 cm$^{-1}$, about 1182 cm$^{-1}$, about 1105 cm$^{-1}$, about 1049 cm$^{-1}$, and about 902 cm$^{-1}$.

Example 5

The mixture of acyclovir (10 g) and water (200 ml) was heated to 90° C., stirred to obtain a clear solution and filtered. The filtrate was cooled to 20~25° C., held for 10 h to precipitate crystal, and then filtered. The resulting solid was dried at 100° C. for 5 h and then placed under the circumstance of 80% relative humidity of air for 8 hours to obtain acyclovir crystal (9.5 g), with purity of 99.5% by HPLC. The solid was ground into power of 200 mesh in size. The X-ray powder diffraction pattern of the product obtained with Cu-Kα radiation exhibited characteristic peaks at 2θ and interplanar spacings (d value) of about 7.0(12.7), about 10.5(8.4), about 13.1(6.8), about 16.1(5.5), about 18.3(4.9), about 21.0(4.2), about 24.9 (3.7), about 26.2(3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 cm$^{-1}$, about 3471 cm$^{-1}$, about 3438 cm$^{-1}$, about 3294 cm$^{-1}$, about 3180 cm$^{-1}$, about 2854 cm$^{-1}$, about 2698 cm$^{-1}$, about 1716 cm$^{-1}$, about 1631 cm$^{-1}$, about 1610 cm$^{-1}$, about 1483 cm$^{-1}$, about 1388 cm$^{-1}$, about 1182 cm$^{-1}$, about 1105 cm$^{-1}$, about 1049 cm$^{-1}$, and about 902 cm$^{-1}$.

Example 6

The mixture of acyclovir (10 g) and water (200 ml) was heated to 90° C., stirred to obtain a dear solution and filtered. The filtrate was cooled to 20~25° C., held for 10 h to precipitate crystal, and then filtered. The resulting solid was dried at 120° C. for 5 h and then placed under the circumstance of 60% relative humidity of air for 10 hours to obtain acyclovir crystal (9.5 g), with purity of 99.5% by HPLC. The solid was ground into power of 200 mesh in size. The X-ray powder diffraction pattern of the product obtained with Cu-Kα radiation exhibited characteristic peaks at 2θ and interplanar spacings (d value) of about 7.0(12.7), about 10.5(8.4). about 13.1(6.8), about 16.1(5.5), about 18.3(4.9), about 21.0(4.2), about 24.9 (3.7), about 26.2(3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 $cm^{-1}$, about 3471 $cm^{-1}$, about 3438 $cm^{-1}$, about 3294 $cm^{-1}$, about 3180 $cm^{-1}$, about 2854 $cm^{-1}$, about 2698 $cm^{-1}$, about 1716 $cm^{-1}$, about 1631 $cm^{-1}$, about 1610 $cm^{-1}$, about 1483 $cm^{-1}$, about 1388 $cm^{-1}$, about 1182 $cm^{-1}$, about 1105 $cm^{-1}$, about 1049 $cm^{-1}$, and about 902 $cm^{-1}$.

Example 7

The mixture of acyclovir (10 g) and water (200 ml) was heated to 90° C., stirred to obtain a clear solution and filtered. The filtrate was cooled to 20~25° C., held for 10 h to precipitate crystal. and then filtered. The resulting solid was dried at 150° C. for 3 h and then placed under the circumstance of 70% relative humidity of air for 10 hours to obtain acyclovir crystal (9.5 g), with purity of 99.5% by HPLC. The solid was ground into power of 200 mesh in size. The X-ray powder diffraction pattern of the product obtained with Cu-Kα radiation exhibited characteristic peaks at 2θ and interplanar spacings (d value) of about 7.0(12.7), about 10.5(8.4), about 13.1(6.8), about 16.1(5.5), about 18.3(4.9), about 21.0(4.2), about 24.9 (3.7), about 26.2(3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 $cm^{-1}$, about 3471 $cm^{-1}$, about 3438 $cm^{-1}$, about 3294 $cm^{-1}$, about 3180 $cm^{-1}$, about 2854 $cm^{-1}$, about 2698 $cm^{-1}$, about 1716 $cm^{-1}$, about 1631 $cm^{-1}$, about 1610 $cm^{-1}$, about 1483 $cm^{-1}$, about 1388 $cm^{-1}$, about 1182 $cm^{-1}$, about 1105 $cm^{-1}$, about 1049 $cm^{-1}$, and about 902 $cm^{-1}$.

Example 8

The mixture of acyclovir (10 g) and water (150 ml) was heated to 90° C., stirred to obtain a clear solution and filtered. The filtrate was cooled to 0° C., held for 12 h to precipitate crystal, and then filtered. The resulting solid was dried under vacuum at 50° C. for 20 h to obtain acyclovir crystal (9.9 g), with purity of 99.7% by HPLC. The solid was ground into power of 200 mesh in size. The X-ray powder diffraction pattern of the product obtained with Cu-Kα radiation exhibited characteristic peaks at 2θ and interplanar spacings (d value) of about 7.0(12.7), about 10.5(8.4), about 13.1(6.8), about 16.1(5.5), about 18.3(4.9), about 21.0(4.2), about 24.9 (3.7), about 26.2(3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 $cm^{-1}$, about 3471 $cm^{-1}$, about 3438 $cm^{-1}$, about 3294 $cm^{-1}$, about 3180 $cm^{-1}$, about 2854 $cm^{-1}$, about 2698 $cm^{-1}$, about 1716 $cm^{-1}$, about 1631 $cm^{-1}$, about 1610 $cm^{-1}$, about 1483 $cm^{-1}$, about 1388 $cm^{-1}$, about 1182 $cm^{-1}$, about 1105 $cm^{-1}$, about 1049 $cm^{-1}$, and about 902 $cm^{-1}$.

Example 9

The mixture of acyclovir (10 g) and water (150 ml) was heated to 10020 C., stirred to obtain a clear solution and filtered. The filtrate was cooled to 0° C., held for 24 hours to precipitate crystal, and then filtered. The resulting solid was dried under vacuum at 50° C. for 20 h to obtain acyclovir crystal (9.9 g), with purity of 99.7% by HPLC. The solid was ground into power of 200 mesh in size. The X-ray powder diffraction pattern of the product obtained with Cu-Kα radiation exhibited characteristic peaks at 2θ and interplanar spacings (d value) of about 7.0(12.7), about 10.5(8.4), about 13.1 (6.8), about 16.1(5.5), about 18.3(4.9), about 21.0(4.2), about 24.9(3.7), about 26.2(3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 $cm^{-1}$, about 3471 $cm^{-1}$, about 3438 $cm^{-1}$, about 3294 $cm^{-1}$, about 3180 $cm^{-1}$, about 2854 $cm^{-1}$, about 2698 $cm^{-1}$, about 1716 $cm^{-1}$, about 1631 $cm^{-1}$, about 1610 $cm^{-1}$, about 1483 $cm^{-1}$, about 1388 $cm^{-1}$, about 1182 $cm^{-1}$, about 1105 $cm^{-1}$, about 1049 $cm^{-1}$, and about 902 $cm^{-1}$.

Example 10

The mixture of acyclovir (10 g) and water (150 ml) was heated to 90° C., stirred to obtain a clear solution and filtered. The filtrate was cooled to 30° C., held for 12 h to precipitate crystal. and then filtered. The solid was dried under vacuum at 50° C. for 24 h to obtain acyclovir crystal (9.7 g), with purity of 99.7% by HPLC. The solid was ground into power of 200 mesh in size. The X-ray powder diffraction pattern of the product obtained with Cu-Kα radiation exhibited characteristic peaks at 2θ and interplanar spacings (d value) of about 7.0(12.7), about 10.5(8.4), about 13.1(6.8), about 16.1(5.5), about 18.3(4.9), about 21.0(4.2), about 24.9(3.7), about 26.2 (3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 $cm^{-1}$, about 3471 $cm^{-1}$, about 3438 $cm^{-1}$, about 3294 $cm^{-1}$, about 3180 $cm^{-1}$, about 2854 $cm^{-1}$, about 2698 $cm^{-1}$, about 1716 $cm^{-1}$, about 1631 $cm^{-1}$, about 1610 $cm^{-1}$, about 1483 $cm^{-1}$, about 1388 $cm^{-1}$, about 1182 $cm^{-1}$, about 1105 $cm^{-1}$, about 1049 $cm^{-1}$, and about 902 $cm^{-1}$.

Example 11

The mixture of acyclovir (10 g) and water (150 ml) was heated to 90° C., stirred to obtain a clear solution and filtered. The filtrate was cooled to 30° C., held for 24 h to precipitate crystal, and then filtered. The resulting solid was dried under vacuum at 50° C. for 12 h to obtain acyclovir crystal (9.8 g), with purity of 99.8% by HPLC. The solid was ground into power of 200 mesh in size. The X-ray powder diffraction pattern of the product obtained with Cu-Kα radiation exhibited characteristic peaks at 2θ and interplanar spacings (d value) of about 7.0(12,7), about 10.5(8.4), about 13.1(6.8), about 16.1(5.5), about 18.3(4.9), about 21.0(4.2), about 24.9 (3.7), about 26.2(3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 cm$^{-1}$, about 3471 cm$^{-1}$, about 3438 cm$^{-1}$, about 3294 cm$^{-1}$, about 3180 cm$^{-1}$, about 2854 cm$^{-1}$, about 2698 cm$^{-1}$, about 1716 cm$^{-1}$, about 1631 cm$^{-1}$, about 1610 cm$^{-1}$, about 1483 cm$^{-1}$, about 1388 cm$^{-1}$, about 1182 cm$^{-1}$, about 1105 cm$^{-1}$, about 1049 cm$^{-1}$, and about 902 cm$^{-1}$.

Example 12

The mixture of acyclovir (10 g) and water (200 ml) was heated to 50° C., stirred to obtain a clear solution and filtered. The filtrate was cooled to 0° C., held for 1 h to precipitate crystal, and then filtrated. The resulting solid was dried under vacuum at 50° C. for 24 h to obtain acyclovir crystal (9.6 g), with purity of 99.8% by HPLC. The solid was ground into power of 200 mesh in size. The X-ray powder diffraction pattern of the product obtained with Cu-Kα radiation exhibited characteristic peaks at 2θ and interplanar spacings (d value) of about 7.0(12.7), about 10.5(8.4), about 13.1(6.8), about 16.1(5.5), about 18.3(4.9), about 21.0(4.2), about 24.9 (3.7), about 26.2(3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 cm$^{-1}$, about 3471 cm$^{-1}$, about 3438 cm$^{-1}$, about 3294 cm$^{-1}$, about 3180 cm$^{-1}$, about 2854 cm$^{-1}$, about 2698 cm$^{-1}$, about 1716 cm$^{-1}$, about 1631 cm$^{-1}$, about 1610 cm$^{-1}$, about 1483 cm$^{-1}$, about 1388 cm$^{-1}$, about 1182 cm$^{-1}$, about 1105 cm$^{-1}$, about 1049 cm$^{-1}$, and about 902 cm$^{-1}$.

Example 13

The mixture of acyclovir (10 g) and water (150 ml) was heated to 90° C., stirred to obtain a clear solution and filtered. The filtrate was cooled to 20° C., held for 5 h to precipitate crystal, and then filtered. The resulting solid was dried under vacuum at 50 20 C. for 20 h to obtain acyclovir crystal (9.9 g), with purity of 99.7% by HPLC. The solid was ground into power of 100 mesh in size. The X-ray powder diffraction pattern of the product obtained with Cu-Kα radiation exhibited characteristic peaks at 2θ and interplanar spacings (d value) of about 7.0(12.7), about 10.5(8.4), about 13.1(6.8), about 16.1(5.5), about 18.3(4.9), about 21.0(4.2), about 24.9 (3.7), about 26.2(3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 cm$^{-1}$, about 3471 cm$^{-1}$, about 3438 cm$^{-1}$, about 3294 cm$^{-1}$, about 3180 cm$^{-1}$, about 2854 cm$^{-1}$, about 2698 cm$^{-1}$, about 1716 cm$^{-1}$, about 1631 cm$^{-1}$, about 1610 cm$^{-1}$, about 1483 cm$^{-1}$, about 1388 cm$^{-1}$, about 1182 cm$^{-1}$, about 1105 cm$^{-1}$, about 1049 cm$^{-1}$, and about 902 cm$^{-1}$.

Example 14

The mixture of acyclovir (10 g) and water (100 ml) was heated to 98 ° C., stirred to obtain a clear solution and filtered. The filtrate was cooled to 20° C., held for 5 h to precipitate crystal, and then filtered. The resulting solid was dried at 150° C. for 0.5 h to obtain acyclovir crystal (9.7 g), with purity of 99.7% by HPLC. The solid was ground into power of 100 mesh in size. The X-ray powder diffraction pattern of the product obtained with Cu-Kα radiation exhibited characteristic peaks at 2θ and interplanar spacings (d value) of about 7.0(12.7), about 10.5(8.4), about 13.1(6.8), about 16.1(5.5), about 18.3(4.9), about 21.0(4.2), about 24.9(3.7), about 26.2 (3.4), and about 29.2(3.0). The product had a weight-loss as measured by Thermogravimetric Analysis (TGA) of about 5.1% by weight. The infrared absorption spectrum (KBr pellet) of the product showed absorption peaks at about 3522 cm$^{-1}$, about 3471 cm$^{-1}$, about 3438 cm$^{-1}$, about 3294 cm$^{-1}$, about 3180 cm$^{-1}$, about 2854 cm$^{-1}$, about 2698 cm$^{-1}$, about 1716 cm$^{-1}$, about 1631 cm$^{-1}$, about 1610 cm$^{-1}$, about 1483 cm$^{-1}$, about 1388 cm$^{-1}$, about 1182 cm$^{-1}$, about 1105 cm$^{-1}$, about 1049 cm$^{-1}$, and about 902 cm$^{-1}$.

Example 15

The mixture of acyclovir (10 g) and water (200 ml) was heated to 90° C., stirred to obtain a clear solution and filtered. The filtrate was cooled to 20–25° C., held for 10 h to precipitate crystal, and then filtered. The resulting solid was placed under the room temperature condition for 24 h to obtain acyclovir crystal (9.9 g), with purity of 99.5% by HPLC. The solid was ground into power of 200 mesh in size. The X-ray powder diffraction pattern of the product obtained with Cu-Kα radiation exhibited characteristic peaks at 2θ and interplanar spacings (d value) of about 7.0(12.7), about 10.5(8.4), about 13.1(6.8), about 16.1(5.5), about 18.3(4.9), about 21.0 (4.2), about 24.9(3.7), about 26.2(3.4), and about 29.2(3.0). The product had a weight-loss as measured by Thermogravimetric Analysis (TG) of about 5.1% by weight. The infrared absorption spectrum (KBr pellet) of the product showed absorption peaks at about 3522 cm$^{-1}$, about 3471 cm$^{-1}$, about 3438 cm$^{-1}$, about 3294 cm$^{-1}$, about 3180 cm$^{-1}$, about 2854 cm$^{-1}$, about 2698 cm$^{-1}$, about 1716 cm$^{-1}$, about 1631 cm$^{-1}$, about 1610 cm$^{-1}$, about 1483 cm$^{-1}$, about 1388 cm$^{-1}$, about 1182 cm$^{-1}$, about 1105 cm$^{-1}$, about 1049 cm$^{-1}$, and about 902 cm$^{-1}$.

What is claimed is:

1. A method for preparing an acyclovir 2/3 hydrate, the method comprising:

mixing acyclovir with water at a weight ratio of from 1:5 to 1:50;

dissolving the acyclovir in water at 50-100° C. thereby obtaining an acyclovir water solution;

subjecting the acyclovir water solution to filtration;

cooling the filtrate to 0-30° C. to precipitate crystals;

collecting the crystals by filtration; and drying the crystals at 50-150° C. for 0.5-24 hours, thereby obtaining the acyclovir 2/3 hydrate, wherein the acyclovir 2/3 hydrate has the following characteristic peaks expressed in terms of 2θ and interplanar spacings d value in the X-ray powder diffraction pattern obtained with Cu-Kα radiation:

| Peak | 2θ(°) | Interplanar spacing d (Å) |
|---|---|---|
| 1 | about 7.0 | about 12.7 |
| 2 | about 10.5 | about 8.4 |
| 3 | about 13.1 | about 6.8 |
| 4 | about 16.1 | about 5.5 |
| 5 | about 18.3 | about 4.9 |
| 6 | about 21.0 | about 4.2 |
| 7 | about 24.9 | about 3.7 |
| 8 | about 26.2 | about 3.4 |
| 9 | about 29.2 | about 3.0 | and wherein the acyclovir 2/3 hydrate has a weight-loss as measured by Thermogravimetric Analysis of 5.1% by weight.

2. The method of claim 1, wherein after the drying step, if the water content of the crystals is below 5.1%, the crystals are placed under a condition with a humidity level that is 60-80% of relative humidity of air for 8-10 hours to obtain the acyclovir 2/3 hydrate.

3. The method of claim 1, wherein the time required for precipitating crystals is 1-24 hours.

4. The method of claim 1, wherein the acyclovir and water are mixed at a weight ratio of from 1:10 to 1:15.

5. The method of claim 1, wherein the filtrate is cooled to 20-30° C. and held for 4-10 hours to precipitate the crystals.

6. The method of claim 1, wherein the crystals are dried at 50-100° C. for 5-12 hours.

7. The method of claim 3, wherein the crystals are dried at 50-100° C. for 0.5-24 hours to obtain the acyclovir 2/3 hydrate.

8. The method of claim 1, wherein the acyclovir 2/3 hydrate of has absorption peaks at about 3522 $cm^{-1}$, about 3471 $cm^{-1}$, about 3438 $cm^{-1}$, about 3294 $cm^{-1}$, about 3180 $cm^{-1}$, about 2854 $cm^{-1}$, about 2698 $cm^{-1}$, about 1716 $cm^{-1}$, about 1631 $cm^{-1}$, about 1610 $cm^{-1}$, about 1483 $cm^{-1}$, about 1388 $cm^{-1}$, about 1182 $cm^{-1}$, about 1105 $cm^{-1}$, about 1049 $cm^{-1}$, and about 902 $cm^{-1}$ in the infrared absorption spectrum (KBr pellet).

\* \* \* \* \*